(12) United States Patent
Evans et al.

(10) Patent No.: US 8,534,871 B2
(45) Date of Patent: Sep. 17, 2013

(54) LIGHT PROJECTOR

(75) Inventors: Kate Evans, Wallingford (GB); Jan Paoli, Northamptonshire (GB)

(73) Assignee: Quincom Limited (GB)

( * ) Notice: Subject to any disclaimer, the term of this patent is extended or adjusted under 35 U.S.C. 154(b) by 187 days.

(21) Appl. No.: 13/201,980

(22) PCT Filed: Mar. 2, 2010

(86) PCT No.: PCT/GB2010/050359
§ 371 (c)(1),
(2), (4) Date: Sep. 9, 2011

(87) PCT Pub. No.: WO2010/100482
PCT Pub. Date: Sep. 10, 2010

(65) Prior Publication Data
US 2011/0310613 A1    Dec. 22, 2011

(30) Foreign Application Priority Data

Mar. 6, 2009  (GB) .................................. 0903897.7

(51) Int. Cl.
*F21V 21/15* (2006.01)
*F21V 21/14* (2006.01)
(52) U.S. Cl.
USPC .......................................... 362/272; 362/286

(58) Field of Classification Search
USPC .................................... 362/269–275, 285–289
See application file for complete search history.

(56) References Cited

U.S. PATENT DOCUMENTS

| 4,482,939 | A | * | 11/1984 | Tishman | ........................ | 362/513 |
| 4,930,057 | A | | 5/1990 | Williams | | |
| 4,935,855 | A | * | 6/1990 | Narita | ............................ | 362/286 |
| 2004/0070984 | A1 | | 4/2004 | Smith et al. | | |

FOREIGN PATENT DOCUMENTS

GB    885412    12/1961

\* cited by examiner

*Primary Examiner* — Karabi Guharay
*Assistant Examiner* — Nathaniel Lee
(74) *Attorney, Agent, or Firm* — Hartman Global IP Law; Gary M. Hartman; Domenica N. S. Hartman

(57) ABSTRACT

A light projector (10) for projecting a beam of light (19), which comprises: a housing (16) containing a light source (40) and a projector lens (18), and a drive motor (42), and defining an aperture; and a main shaft (20) extending through the aperture. A flexible and resilient elastomeric coupling (30) links the main shaft (20) to the housing (16) at the aperture. The drive motor (42) is coupled by a drive mechanism (50) to the main shaft (20), so that activation of the drive motor (42) moves the orientation of the housing relative to the longitudinal axis of the main shaft (20). Consequently a light beam (19) from the projector (10) sweeps out a conical surface in space around that longitudinal axis.

14 Claims, 3 Drawing Sheets

LIGHT PROJECTOR

CROSS-REFERENCE TO RELATED APPLICATIONS

This application claims the benefit of International Application No. PCT/GB2010/050359 filed Mar. 2, 2010, having a claim of priority to GB patent application number 09 03897.7, filed Mar. 6, 2009.

The present invention relates to a light projector for projecting a beam of light, where the orientation of the beam of light can be caused to vary.

According to the present invention there is provided a light projector for projecting a beam of light, the light projector including:

a housing containing a light source and a projector lens, and a drive motor, and defining an aperture;

a main shaft for mounting the housing to a support, the main shaft extending from within the housing to outside the housing through the aperture, and defining a longitudinal axis of the light projector;

a flexible and resilient elastomeric coupling that links the main shaft to the housing at the aperture;

wherein the drive motor is coupled by a drive mechanism to the main shaft, so that activation of the drive motor causes the orientation of the housing to move relative to the longitudinal axis.

Preferably, the elastomeric coupling is in the form of a ring, which extends about the periphery of the aperture. The elastomeric coupling allows for a smooth motion of the housing, for example relative to a supporting structure, by minimizing the number of moving parts used to facilitate rotation of the housing.

Preferably the drive mechanism comprises at least one step-down mechanism to reduce the rate of rotation, for example a plurality of belts and pulleys; and preferably the drive motor is mounted within the housing with a vibration-isolating mounting; these features further ensure quiet and smooth motion of the housing. The drive mechanism may additionally or alternatively include gear wheels to provide the step-down of speed. Where gear wheels are used, the drive mechanism preferably also includes a belt and pulleys mechanism. In particular the drive mechanism may enable the rotational speed to be stepped down by a large factor, preferably more than 50, more preferably at least 100, and more preferably at least 500, for example 850. This ensures that the drive motor can run at a high speed, while the housing moves much more slowly. For example with a step down factor of 850 the motor can run at 56 rotations per second, while the housing is driven at only 4 rpm.

As the drive motor actuates the drive mechanism, the orientation of the housing, and therefore the light source and the projector lens, follows a conical path. The flexible and resilient elastomeric coupling provides essentially friction-free movement of the housing relative to the main shaft. This avoids the need for any sliding or rolling relative movement between components, which can be affected by friction; the elastomeric coupling therefore eliminates the risk of judder, enhancing the smooth motion of the housing relative to the support. The housing itself does not rotate relative to the main shaft, but its orientation varies.

Preferably the light projector also incorporates a base unit to which the main shaft is fixed, so that the base unit constitutes the support for the light projector. Such a base unit may enclose power supply elements such as batteries, and may enclose electronic controls such as switches for activation of both the light source and of the drive motor. The power source may be disposable batteries or rechargeable batteries. Further the base unit may include photovoltaic cells to charge the batteries during the day. There is also a plug whereby the base may be plugged into a mains power source. As an alternative to using a base unit, the light projector may be mounted directly onto another support such as a wall or wall bracket.

The light projector may be set up so as to project a spot of light on to a ceiling in the vicinity of a bed where the user wishes to sleep. The actuation of the drive motor causes of the spot of light to follow an elliptical path, moving slowly and smoothly, in a controlled manner, along this path. A user watching this moving spot of light is thereby caused to relax, and is induced to fall asleep because the movement is smooth and controlled. Although the light can be projected onto a ceiling, it could equally well be projected onto a wall or any other suitable and convenient surface. In particular but not exclusively, the projector can be used to aid persons suffering from sleep disorders, such as insomnia.

The lens support may be removable from the housing so that different types of lenses may be used, for example with different focal lengths. The projector may include a shaped aperture so that the lens can project a defined shape, such as a star, oval or cartoon character, which being aesthetically pleasing to a user may further assist in inducing sleep. Projecting familiar shapes, such as a teddy bear, onto a surface may be particularly useful when trying to get children to sleep.

The light projector may also include means to adjust the brightness of the light source, for example to accommodate variations in ambient light intensity, either automatically or under user control. For example the brightness control may be linked to a light sensor sensing the brightness of ambient light. The brightness may for example be adjusted by pulse width modulation, but other adjustments are possible, for example using variable resistors. The brightness may be constant, or varying for example in a linear or sinusoidal fashion with time, or may be pulsed.

It is also envisaged that the housing may include a motion sensor switch, such that when the housing is knocked or flicked with a finger, the switch is activated to start movement of the housing. In an alternative arrangement, where the housing has a base, the motion sensor switch can be in the base.

In a preferred embodiment a single switch in a base unit enables the light projector to be controlled, to adjust brightness and mode (constant or pulsing brightness). For example repeated pressing of this switch may cycle through various different options. The base unit may also include a display to indicate the level of brightness that is being selected. This may comprise an array of illuminated dots. In a preferred embodiment this array is visible through a translucent portion of the base unit, so that the array is visible only when illuminated.

The invention will now be further and more particularly described, by way of example only, and with reference to the accompanying drawings in which.

Figure 1:
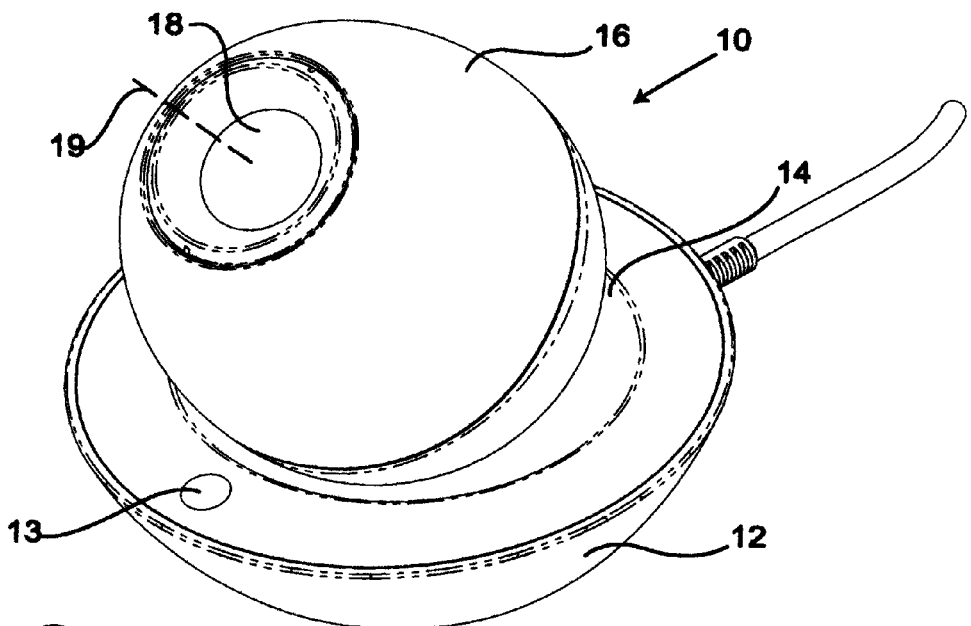
FIG. 1 shows a perspective view of a light projector of the invention, comprising a projector housing and a base unit.

Referring now to FIG. 1, a light projector 10 of the invention comprises a base unit 12 provided with a push button 13, and defining a part-spherical recess 14 in its upper surface. A projector housing 16, which is generally egg-shaped, is mounted in this recess 14 by means of a main shaft 20 (shown in FIG. 2). The housing 16 has a broader end and a narrower end, and at the narrower end is a projector lens 18 for projecting a beam of light indicated by the broken line 19.

Figure 2:
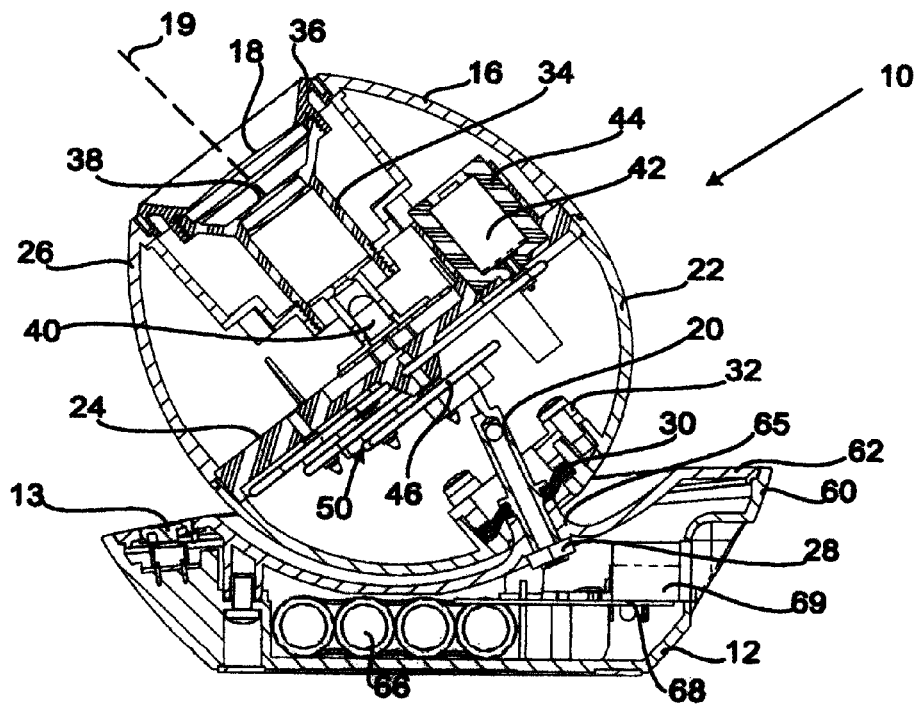
FIG. 2 shows a cross-sectional view through the light projector of FIG. 1.
Figure 3:
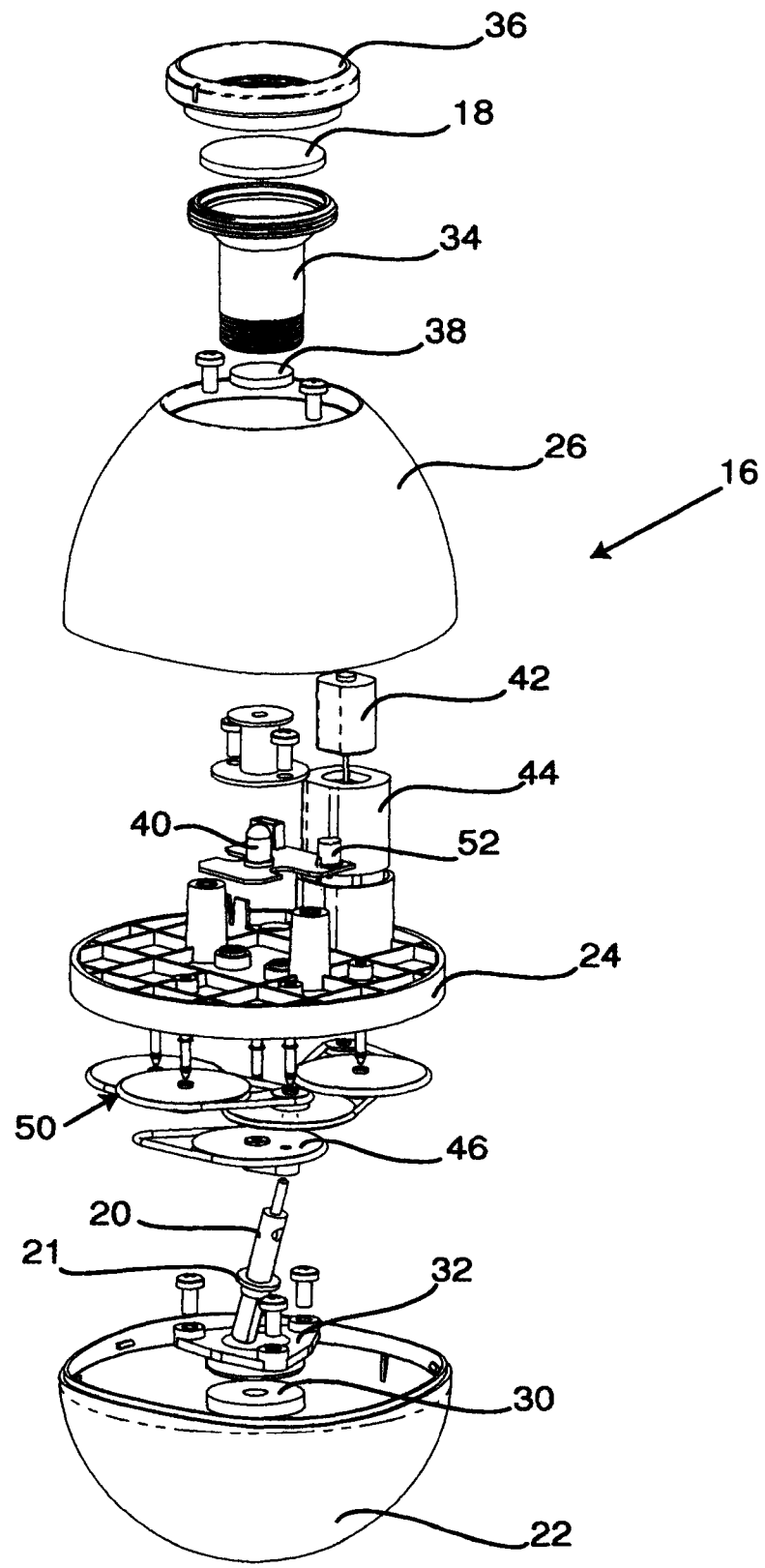
FIG. 3 shows an exploded perspective view of the projector housing of the light projector of FIG. 1.

Referring now to FIGS. 2 and 3, the projector housing 16 comprises a bottom half 22 with an aperture at its base, a circular support plate 24, and a top half 26. The main shaft 20 is fixed by a nut 28 rigidly to the base unit 12; and is fixed to the bottom half 22 of the housing 16 by a resilient elastomeric disc 30 whose periphery is secured by a retaining ring 32. A peripheral flange 21 on the main shaft 20 abuts the upper surface of the elastomeric disc 30. Hence the main shaft 20 extends through the aperture in the base of the bottom half 22, and so within the housing 16. The top half 26 defines, at its narrower end, an aperture in which locates a lens holder 34 and a lens ring 36 that support the projector lens 18 and a second projector lens 38. The lens holder 34 may be demountable from the housing 16 so that lenses can be changed if required.

The circular support plate 24 carries, on its upper surface, a white LED light source 40, and a motor 42 within an isolating motor mount 44, the motor 42 having a drive shaft that extends through to the opposite surface of the support plate 24. The top end of the main shaft 20 is connected pivotally and eccentrically to a drive pulley 46 whose rotation axis is at the centre of the support plate 24. As shown more clearly in FIG. 3, the drive shaft of the motor 42 is connected to the drive pulley 46 by a drive mechanism 50 that consists of several pulleys and drive belts (in this case there are four drive belts each going around one small pulley and one large pulley, to provide a step down in speed), providing an overall step-down factor of 850 in this embodiment. As shown in FIG. 3 the support plate 24 also carries a motion sensor switch 52.

Figure 4:
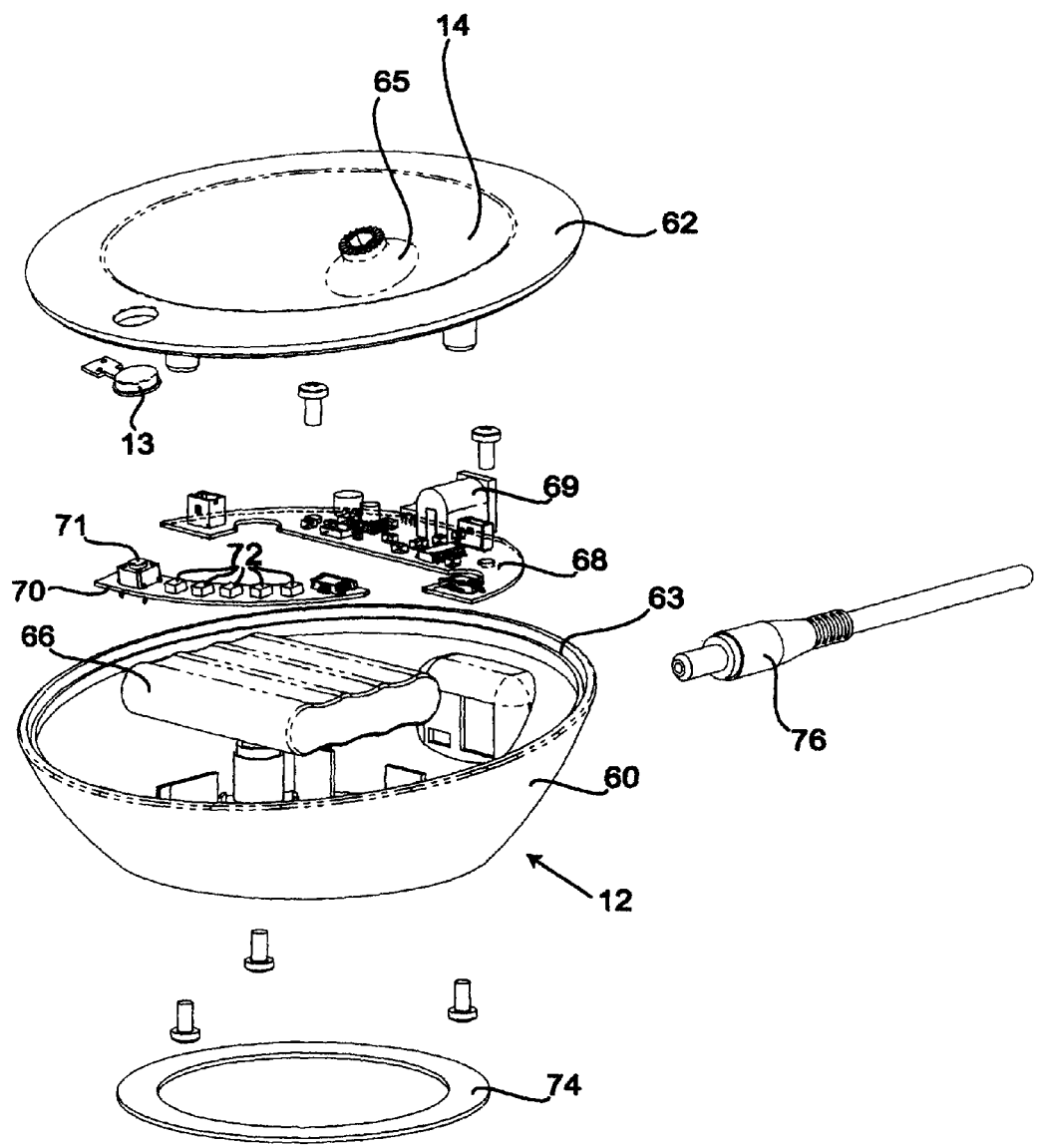
FIG. 4 shows an exploded perspective view of the base unit of the light projector of FIG. 1.

Referring now to FIGS. 2 and 4, the base unit 12 consists of a dish-shaped base part 60 and a cover part 62 which defines the recess 14 and which fits into the top of the base part 60 resting on a circumferential ledge 63. The cover part 62 also defines a projecting boss 65 within the recess 14, through which the main shaft 20 extends; in this embodiment the central part of the elastomeric disc 30 is therefore clamped between the top of the projecting boss 65 and the peripheral flange 21 on the main shaft 20. The base part 60 encloses a battery pack 66; a printed circuit board 68 with an electronic circuit to control operation of the light projector 10, and including a DC power supply socket 69; and a secondary printed circuit board 70 carrying a switch 71 actuated by the push button 13 and a linear array of small LEDs 72. The cover part 62 is translucent, so that illumination of the LEDs 72 is visible. The base unit 12 is also provided with a foam ring 74 which is adhered to its underside. A low voltage supply cable 76 can be plugged into the base unit 12 to connect to the supply socket 69 and to maintain the charge in the battery pack 66.

Although a dish shaped support is described, the support may be any shape. Further, although the device has been described as having a battery pack, individual replaceable batteries may be used, for example rechargeable batteries. Other power sources may be used, for example photovoltaic cells may be used to charge the device during daylight hours. In general the use of batteries—whether charged via a cable 76 from the mains or by photovoltaic cells—is desirable, so the projector can be portable.

Operation of the light projector 10, in this example, can be initiated by tapping the projector housing 16. The motion sensor switch 52 senses this tap, and activates both the LED light source 40 and the motor 42. A light beam 19 is therefore projected, and can for example be arranged to be incident on the ceiling above the user's bed. The resulting light spot follows an elliptical path because the axis of the light beam 19 is at an angle of about 15° to the fixed axis of the main shaft 20; the motor 42 gradually rotates the drive pulley 46, and since the base of the bottom half 22 is substantially fixed by the elastomeric disc 30 while the top end of the main shaft 20 is fixed, the result is that the centre of the support plate 24 is driven along a circular path concentric with the axis of the main shaft 20. Hence the light beam 19 sweeps out a conical surface in space. In principle this rotation of the light beam 19 could be at any desired rate, but in this example it rotates at 4 rpm.

If the user wishes to adjust the brightness of the light beam 19, this can be achieved using the push button 13. The first brief depression of the push button 13 gives a display indicating the current brightness setting, and repeated depression of this button 13 then cycling through a range of options: a range of different brightness levels indicated (as the button 13 is depressed) by illuminating one or more of the display LEDs 72. If the push button 13 is depressed and held down (e.g. for more than 2 s) then the mode changes to a sequence of pulses of the light beam 19, indicated by correspondingly pulsing one or more of the display LEDs 72; or if the mode is already providing pulses, then when the push button 13 is depressed and held down the mode will change back to steady illumination. It will be appreciated that may be a wide range of different variations, for example the brightness of the light beam 19 might instead be gradually varied in a sinusoidal or linear fashion with time. In this example, when the button 13 is not depressed, after a short period of time the display LEDs 72 switch off, and there is no visible trace of the display on the base unit 12.

The user, lying in bed and watching the moving light spot, becomes relaxed and eventually falls asleep. Typically the light projector 10 operates for a fixed period of time, for example 30 minutes, and then automatically switches off. Alternatively the user may, after a period of time, switch off the light projector 10 either by tapping the button 13 or by tapping the projector housing 16. The motor 42 may be provided with digital speed control to vary the speed as required by the user so that the movement has the best effect for sending them to sleep. For example the housing may initially be driven at 4 rpm, and then after for example a period such as 1 to 2 minutes the speed reduces to 3 rpm, and then after a further period to 2 rpm, and then after a further period the motor stops. This may assist the user to fall asleep because as the user gets drowsier, the rate of rotation can be reduced because brain activity is slowing down.

It will be appreciated that the description given above is by way of example only, and that a light projector may differ from that described above while remaining within the scope of the present invention. It is nevertheless desirable, where a base unit is provided, that the main shaft 20 should be inclined from the vertical, so that the centre of the projected light path can be aimed at a convenient position above the user's head. The provision of the multistage belt and pulley system not only provides a significant speed reduction ratio, but provides smooth and quiet operation, so that the light projector makes very little noise. Not only is the motor 42 preferably surrounded by a sound-isolating motor mount 44, but the support plate 24 may also include other sound damping or vibration isolating components to reduce the noise of the motor even further. Providing the projector with an opaque housing (the projector housing 16) is generally desirable, as it enhances the apparent simplicity of the projector; but as an alternative the projector housing might be at least partly transparent so that the mechanism is visible.

As described above the slow rotational movement of the projector 10 is brought about by the high-speed motor 42, combined with a large step-down ratio achieved by the drive mechanism 50. In a modification the projector may instead incorporate a motor that runs at somewhat lower speed, so reducing the required step-down ratio. For example a low-voltage DC high-speed motor that would normally operate at 2000 rpm or more may be driven at say 200 rpm, and with sufficient torque to drive the projector, by powering it with a negative resistance drive to counteract the voltage drop in the windings. Substantially constant rotation speed can be achieved by a feedback loop that senses current pulses from the commutator. In this case the drive mechanism 50 does not have to provide such a large step-down ratio: the step-down ratio might be 50 rather than 850.

In the light projector 10 described above, the elastomeric disc 30 is connected to the main shaft 20 by virtue of the disc 30 being clamped between the peripheral flange 21 (on the main shaft 20) and the projecting boss 65 (on the base unit 12). In a modification the elastomeric disc may instead be moulded onto the shaft, this being particularly appropriate if the main shaft is of a plastic material. Instead of fixing the main shaft onto the base unit by a nut 28, the main shaft in this case may be simply clipped onto the base unit.

The spot of light produced by the light source 40 may be white, but alternatively it may be a different colour such as blue or red. The lenses 18 and 38, in this example, produce a circular light spot, but alternatively the projector may be arranged to produce a light spot of a different shape, such as a cross shape or star shape; this may require the lenses 18 and 38 to be adjusted to ensure the light is focused on the ceiling. It will also be appreciated that there may be a different number of lenses in the projector. It will also be appreciated that the brightness of the light may be adjusted automatically, by providing a light sensor to sense the level of ambient light, and adjusting the brightness of the LED 40 accordingly.

Although individual embodiments are discussed, it is to be understood that combinations of the individual embodiments form part of the invention as claimed and described. Further those skilled in the art will appreciate that various modifications may be made to the invention without departing significantly from the spirit and scope of the inventions as described and claimed.

The invention claimed is:

1. A light projector for projecting a beam of light, the light projector including:

a housing containing a light source and a projector lens, and a drive motor, and defining an aperture;

a main shaft for mounting the housing to a support, the main shaft extending from within the housing to outside the housing through the aperture, and defining a longitudinal axis of the light projector;

a flexible and resilient elastomeric coupling that links the main shaft to the housing at the aperture;

wherein the drive motor is coupled by a drive mechanism to the main shaft, so that activation of the drive motor causes the orientation of the housing to move relative to the longitudinal axis.

2. A light projector as claimed in claim 1 wherein the drive mechanism comprises at least one step-down mechanism.

3. A light projector as claimed in claim 1 wherein the drive mechanism comprises at least one drive belt and pulleys.

4. A light projector as claimed in claim 3 wherein the drive mechanism comprises a plurality of drive belts and pulleys.

5. A light projector as claimed in claim 1 wherein the drive mechanism comprises gear wheels.

6. A light projector as claimed in claim 1 wherein the drive motor is mounted within the housing with a vibration-isolating mounting.

7. A light projector as claimed in claim 1 also comprising means to adjust the brightness of the light source.

8. A light projector as claimed in claim 1 also incorporating a base unit to which the main shaft is fixed, so that the base unit constitutes the support for the light projector.

9. A light projector as claimed in claim 8 wherein the base unit encloses electronic controls for activation of both the light source and of the drive motor.

10. A light projector as claimed in claim 8 comprising a single switch in the base unit to adjust brightness and to change between steady or pulsing light.

11. A light projector as claimed in claim 1 also comprising a display to indicate the level of brightness that is being selected.

12. A light projector as claimed in claim 11 wherein a display to indicate the level of brightness is illuminated behind a translucent element, so that the display is visible only when illuminated.

13. A light projector as claimed in claim 1, wherein the housing includes a motion sensor switch which can be used to activate movement of the housing.

14. The use of a light projector as claimed in claim 1 to induce a user to fall asleep.

* * * * *